(12) United States Patent
Birks et al.

(10) Patent No.: US 7,045,359 B2
(45) Date of Patent: May 16, 2006

(54) METHOD AND APPARATUS TO DETECT A GAS BY MEASURING OZONE DEPLETION

(75) Inventors: John W. Birks, Longmont, CO (US); Mark J. Bollinger, Golden, CO (US)

(73) Assignee: Novanox, LLC, Golden, CO (US)

( * ) Notice: Subject to any disclaimer, the term of this patent is extended or adjusted under 35 U.S.C. 154(b) by 361 days.

(21) Appl. No.: 10/206,464

(22) Filed: Jul. 26, 2002

(65) Prior Publication Data

US 2004/0018630 A1    Jan. 29, 2004

(51) Int. Cl.
*G01N 31/00* (2006.01)

(52) U.S. Cl. ............... 436/118; 436/164; 436/166; 436/172

(58) Field of Classification Search .......... 436/118, 436/164
See application file for complete search history.

(56) References Cited

U.S. PATENT DOCUMENTS

| | | |
|---|---|---|
| 3,528,779 A | 9/1970 | Fontijn |
| 3,904,371 A | 9/1975 | Net et al. |
| 4,240,798 A | 12/1980 | Wendelin et al. |
| 4,277,259 A | 7/1981 | Rounbehler et al. |
| 4,657,744 A | 4/1987 | Howard |
| 4,822,564 A | 4/1989 | Howard |
| 4,849,178 A | 7/1989 | Azuma |
| 5,047,352 A | 9/1991 | Stetter et al. |
| 5,356,818 A | 10/1994 | Johnson |
| 5,922,610 A | 7/1999 | Alving et al. |
| 6,033,368 A | 3/2000 | Gaston, IV et al. |
| 6,096,267 A | 8/2000 | Kishkovich et al. |

(Continued)

FOREIGN PATENT DOCUMENTS

| | | |
|---|---|---|
| EP | 174093 A1 | 3/1986 |
| JP | S51-36342 | 4/1976 |

(Continued)

OTHER PUBLICATIONS

Mok et al. "Reduction of Nitrogen Oxides by Ozonization-Catalysis Hybrid Process", Korean J. Chem. Eng., 21(5), 976-982 (2004).*

(Continued)

*Primary Examiner*—Yelena G. Gakh
(74) *Attorney, Agent, or Firm*—Aileen Law; Patent Law Offices of Rick Martin, P.C.

(57) ABSTRACT

The present invention relates to an apparatus and method for determining the concentration of nitric oxide (NO) in a gas mixture such as air. The gas sample containing NO is mixed with a gas containing ozone ($O_3$), and the change in the ozone concentration is measured after a sufficient time is allowed for the reaction between NO and $O_3$ to take place and destroy a measurable quantity of $O_3$. In the disclosed embodiment, the concentration of ozone is measured using the technique of UV absorption. In this case, the invention has the advantage over other instruments for measuring NO of having absolute calibration based on the known extinction coefficient for ozone at ultraviolet wavelengths. The invention discloses both static and dynamic flow systems, and the NO concentration measurements may be made over a wide pressure range.

29 Claims, 18 Drawing Sheets

U.S. PATENT DOCUMENTS

| | | | |
|---|---|---|---|
| 6,099,480 | A | 8/2000 | Gustafsson |
| 6,100,096 | A | 8/2000 | Bollinger et al. |
| 6,207,460 | B1 | 3/2001 | Kishkovich et al. |
| 6,296,806 | B1 | 10/2001 | Kishkovich et al. |
| 6,346,419 | B1 | 2/2002 | Ryerson et al. |
| 6,635,415 | B1 | 10/2003 | Bollinger et al. ........... 436/116 |

FOREIGN PATENT DOCUMENTS

| | | |
|---|---|---|
| JP | 57173740 | 10/1982 |
| JP | 01248041 | 10/1989 |
| JP | 03282355 | 12/1991 |

OTHER PUBLICATIONS

Allergol Immunopathod (Madr) 2000. 28(3):124-35 (Abstract).

Clin Sci (Lond) 1999, 96(1):67-74 (Abstract).

International Search Report mailed Oct. 1, 2003—International Application No. PCT/US03/22234 filed Jul. 16, 2003.

PCT Written Opinion, date of mailing Aug. 16, 2004 for International Application No. PCT/US03/22234 filed Jul. 16, 2003.

* cited by examiner

US 7,045,359 B2

METHOD AND APPARATUS TO DETECT A GAS BY MEASURING OZONE DEPLETION

FIELD OF INVENTION

The present invention relates to gas analysis, and more particularly to the detection and measurement of nitric oxide (NO) in gases such as air and human breath by measuring ozone depletion.

More generally, this invention applies to the measurement of the concentration of any chemical species in a gas such as air if that gas reacts with ozone at a sufficient rate to cause a measurable change in the ozone concentration. Examples of other chemical species that may be quantified include but are not limited to alkynes and alkenes such as acetylene, ethylene and propylene, compounds commonly found in petrochemical feedstocks.

BACKGROUND OF THE INVENTION

Scientific work over the past decade has demonstrated that the concentration of NO in human breath can be a good indicator of inflammation in the lungs caused by asthma and other respiratory diseases. As a result, there is presently a need for a simple, lightweight, low cost instrument for the measurement of NO in human breath. This invention addresses that need in particular, but is also applicable to the measurement of NO, $NO_2$ $NO_x$, $NO_y$ and various gases that react with ozone that are present in air and other gas mixtures such as cylinders containing compressed gases and petrochemical feedstocks for chemical synthesis.

At present, the concentration of NO in a gas sample such as air is most commonly measured by mixing the gas sample with air or oxygen containing ozone gas at low pressures. In a reaction chamber, nitric oxide molecules react with ozone ($O_3$) molecules, to form nitrogen dioxide ($NO_2$) and oxygen ($O_2$) molecules. A small fraction of those reactions also results in the emission of photons having a red or near-infrared wavelength. The concentration of NO in the gas sample is determined by measuring the intensity of that photon emission. This technique, referred to as the "NO+$O_3$ Chemiluminescence" technique is highly sensitive and widely used in the measurement of NO concentrations in ambient air and in inhaled and exhaled human breath. The principal disadvantages of this technique are: 1) a vacuum pump is required, making the instrument large, heavy and highly consumptive of electrical power; 2) a cooled, red-sensitive photomultiplier tube is required, adding to the bulk and weight of the instrument and making it relatively expensive; and 3) the mixing ratio of ozone required for sensitive detection is high, typically a few percent, and requires a high-voltage (several hundred volts) electrical discharge to produce the ozone, thereby increasing the risk of human exposure to this toxic gas and to the danger of electrical shock.

Another technique for measuring concentrations of NO in air samples involves contacting a gas sample with an alkaline luminol solution. As with the ozone-based method described above, this technique produces chemiluminescence. This approach has the advantage of not requiring a vacuum pump and of detecting photons in the visible region where the photomultiplier tube need not be cooled. However, sensitive detection using this technique requires the use of chromium (VI) oxide ($CrO_3$) to oxidize NO to $NO_2$ prior to contact with the luminol solution, and measures must be taken to eliminate large interferences in the measurement from $CO_2$ and water vapor, both of which are present in exhaled breath at high concentrations.

This invention makes use of the same chemical reaction used in the conventional NO+$O_3$ chemiluminescence instrument commonly used in air pollution monitoring and breath analysis. However, the invention differs significantly from that instrument in that the basis of detection is not chemiluminescence (detection of photons emitted by the reaction). Instead, the invention measures the decrease in the concentration of ozone that occurs in the chemical reaction. Advantages of this invention over the conventional NO+$O_3$ chemiluminescence technique are: 1) the concentration of ozone required is much lower, in the low part-per-million range rather than the percent range; 2) the instrument can be operated at any pressure, such as ambient atmospheric pressure, and therefore does not require a vacuum pump; 3) a photomultiplier tube is not required; and 4) the instrument can be based on the extinction of UV light and, therefore, is potentially self-calibrating, which might eliminate the need for compressed cylinders containing standard concentrations of NO.

SUMMARY OF THE INVENTION

One aspect of the present invention is to provide a simple ozone depletion measurement method and apparatus to detect NO concentration in a test sample.

Another aspect of the present invention is to use known UV instruments to detect levels of $O_3$.

Another aspect of the present invention is to provide a flexible test chamber for use as a portable home test kit for lung disease patients.

Another aspect of the present invention is to provide batch and continuous flow methods and apparatus to measure $O_3$ depletion.

Other aspects of this invention will appear from the following description and appended claims, reference being made to the accompanying drawings forming a part of this specification wherein like reference characters designate corresponding parts in the several views.

A suitable application of the invention is the measurement of the concentration of NO in the inhaled or exhaled air of a human being or other living organism. Another suitable application is the measurement of NO in ambient air for air pollution monitoring and for scientific studies of atmospheric chemistry. The invention also applies to measurements of nitrogen dioxide ($NO_2$) in a gas mixture such as air when $NO_2$ is first reduced to NO via a photolytic or chemical reaction. In ambient air, the invention may be used to measure the sum of NO and $NO_2$ concentrations, commonly referred to as $NO_x$. The invention also applies to the measurement of reactive oxides of nitrogen such as $NO_2$, nitrate radical ($NO_3$), dinitrogen pentoxide ($N_2O_5$), nitrous acid ($HNO_2$), nitric acid ($HNO_3$), peroxynitric acid ($HNO_4$), peroxyacetyl nitrate (PAN), chlorine nitrate ($ClNO_3$) and particulate nitrate, collectively referred to as $NO_y$, either separately or in combination. These nitrogen oxide species may be caused to produce NO in a chemical reaction, as in the reaction at a heated molybdenum oxide surface or in the reaction at a heated gold surface in the presence of a suitable reducing agent such as hydrogen or carbon monoxide (CO). The present invention measures the concentration of NO produced in such reactions.

The invention may be applied to the detection and quantification of any substance that may be treated so as to release gaseous NO. For example, it is known in the art of chromatography that many compounds containing nitrogen can be heated or reacted with other chemicals to produce NO gas. The NO produced by heating or by reaction with other chemicals may be detected and quantified using the invention described here. Similarly, various substances containing nitrogen such as fertilizers and chemicals used as explosives will slowly decompose to release NO gas, and that NO gas can be detected and quantified using this invention. The detection of fertilizers and explosives may be enhanced by heating the sample to increase the rate of release of NO gas.

The invention also applies to the detection and quantification of chemical compounds that do not contain nitrogen themselves but that will react with a nitrogen-containing compound to produce NO gas. An example is the detection and quantification of carbon monoxide (CO) where air containing CO is mixed with a nitrogen-containing compound such as $NO_2$ and heated in the presence of a catalytic surface such as a gold surface to produce NO. The NO thus produced can be detected and quantified using this invention as a means of detecting and quantifying the CO in the air sample.

Before explaining the disclosed embodiment of the present invention in detail, it is to be understood that the invention is not limited in its application to the details of the particular arrangement(s) shown, since the invention is capable of other embodiments. Also, the terminology used herein is for the purpose of description and not of limitation.

DETAILED DESCRIPTION OF THE DRAWINGS

Figure 1:
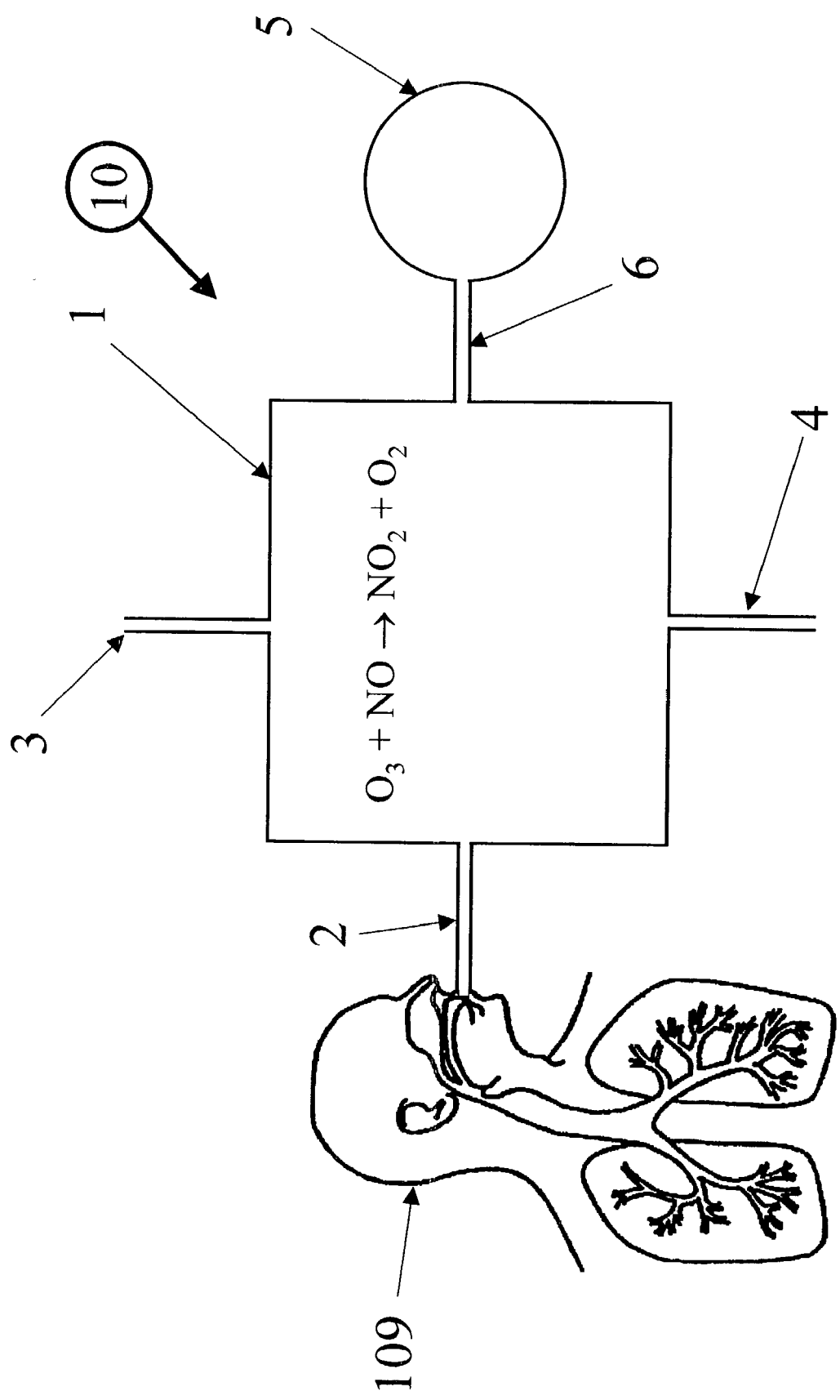
FIG. 1 is a schematic layout of a theoretical test chamber to mix NO and ozone ($O_3$) in a static system.

Referring first to FIG. 1 it is understood that the reaction

$$O_3+NO \rightarrow NO_2+O_2+\text{light energy} \quad \text{(Equation 1)}$$

occurs inside reaction chamber 1. However, the present invention does not measure the light energy as does the prior art. Rather, the present invention measures a decrease in $O_3$ concentration, which equates to a concentration of NO in a test sample. This $O_3$+NO reaction occurs within batch system 10 in reaction chamber 1. First ozone ($O_3$) is added to the test chamber 1 via ozone inlet 3. Generic ozone meter 5 measures the $O_3$ concentration. Then patient 109 exhales a breath sample via sample inlet 2 into the test chamber 1. The test sample contains an unknown amount of NO. Meter 5 measures the concentration of $O_3$ after the $O_3$+NO reaction is sufficiently complete to determine the concentration of NO in the breath sample. Here, connecting tube 6 feeds the ozone meter 5 the gases from the test chamber 1. The exhaust port 4 is opened after the measurements are done. Known in the art are several valving methods to accomplish the above measurements. For example, the test chamber 1 could be run at a vacuum pressure with the appropriate valves at tubes 2, 3 and 4. The above system is an example of a static rather than a continuous flow system.

Practice of the present invention requires knowledge of the reaction rate of NO+$O_3$ and the extinction coefficient for $O_3$; both of which are well known in the art. Alternatively, calibration standards could be used to establish the concentration of NO in the sample.

If the reaction takes place but is not complete, a correction may be applied according to the formula $$[NO]_{sample}=[NO]_{measured}/\{1-\exp(-k[O_3]t)\} \quad \text{(Equation 2)}$$

where $NO_{measured}$ is the concentration of NO measured, $[NO]_{sample}$ is the actual NO concentration in the gas sample, $[O_3]$ is the concentration of $O_3$ and t is the contact time between NO and $O_3$. k is the second order rate constant for the gas-phase reaction of NO with ozone. This calculation assumes pseudo-first order kinetics with $[O_3]>>[NO]$. If this condition does not hold, then one skilled in the art can apply the well-known results of second-order kinetics to correct for the concentration of NO that remains unreacted.

Figure 2:
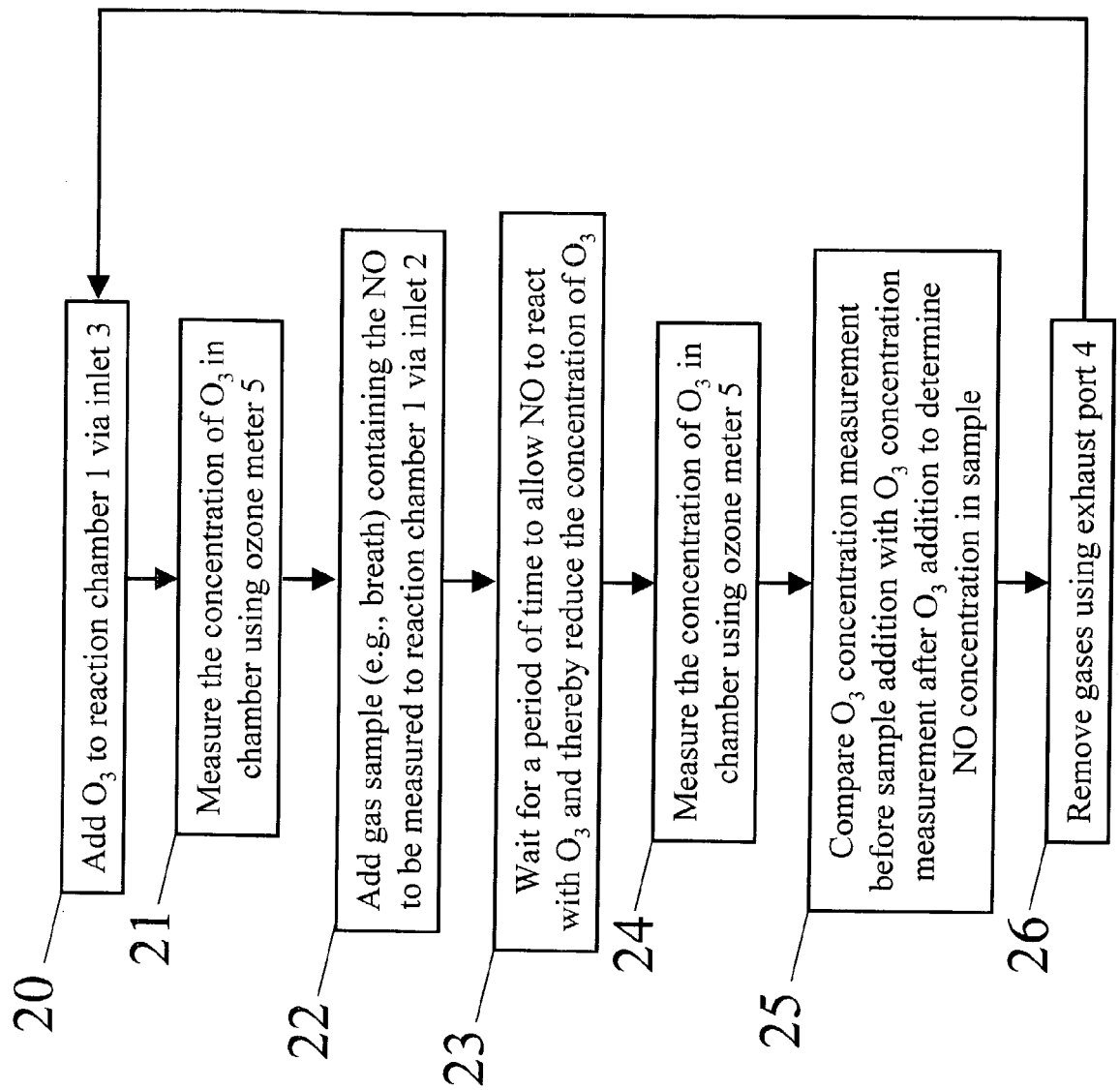
FIG. 2 is a flow chart of the basic steps of one method of ozone detection comprising a static system.

Referring next to FIG. 2 the static or batch process using the FIG. 1 equipment is described. The first step is numbered 20. Step 20 calls for adding $O_3$ to test chamber 1. Step 21 calls for using ozone meter 5 to measure the $O_3$ concentration in the test chamber 1. Step 22 calls for adding an air sample with an unknown concentration of NO in it. FIG. 1 shows the measurement of a human breath sample. Step 23 calls for allowing a period of time to pass to allow the $O_3$ to react with the NO. This reaction decreases the concentration of $O_3$ in test chamber 1. Step 24 calls for the measurement of the $O_3$ concentration after the $O_3$+NO reaction is sufficiently complete. Step 25 calls for a comparative calculation of the O$_3$ concentration before and after the test sample was added into the test chamber 1. The calculation yields actual NO concentration as the below noted example indicates. Step 26 calls for the evacuation of the test chamber 1 to prepare for another measurement. Known in the art are several ways to clear the test chamber 1.

Figure 3:
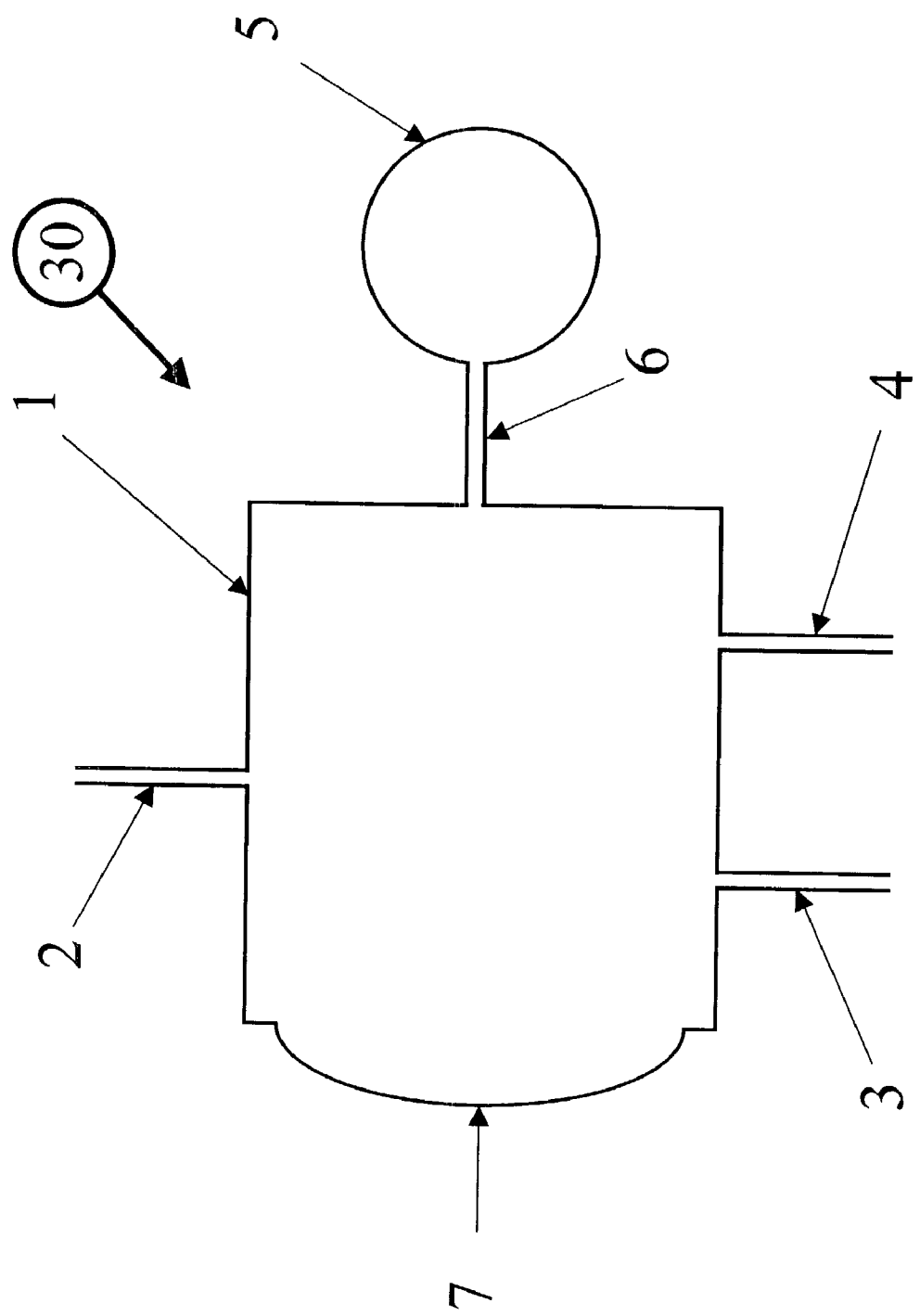
FIG. 3 is a schematic layout of an alternate embodiment chamber having an expandable wall to provide a test chamber that does not require a vacuum or a pressurized environment.

Referring next to FIG. 3 another batch system 30 functions the same as the FIG. 1 system and the FIG. 2 process. The new feature in FIG. 3 is the flexible membrane 7 on at least one side of the test chamber 1. This flexible membrane 7 could also be built as an entirely flexible polymer bag. The benefit of the flexible membrane 7 is to allow a user 109 to blow his breath into inlet tube 2 and expand the flexible membrane 7, assuming all other tubes 3, 4 are short. This expansion eliminates the need for lab equipment to evacuate the test chamber 1 before the test. Thus, the batch test apparatus 30 is suited for an inexpensive home use kit for patients who require daily monitoring of their lung condition.

Figure 4:
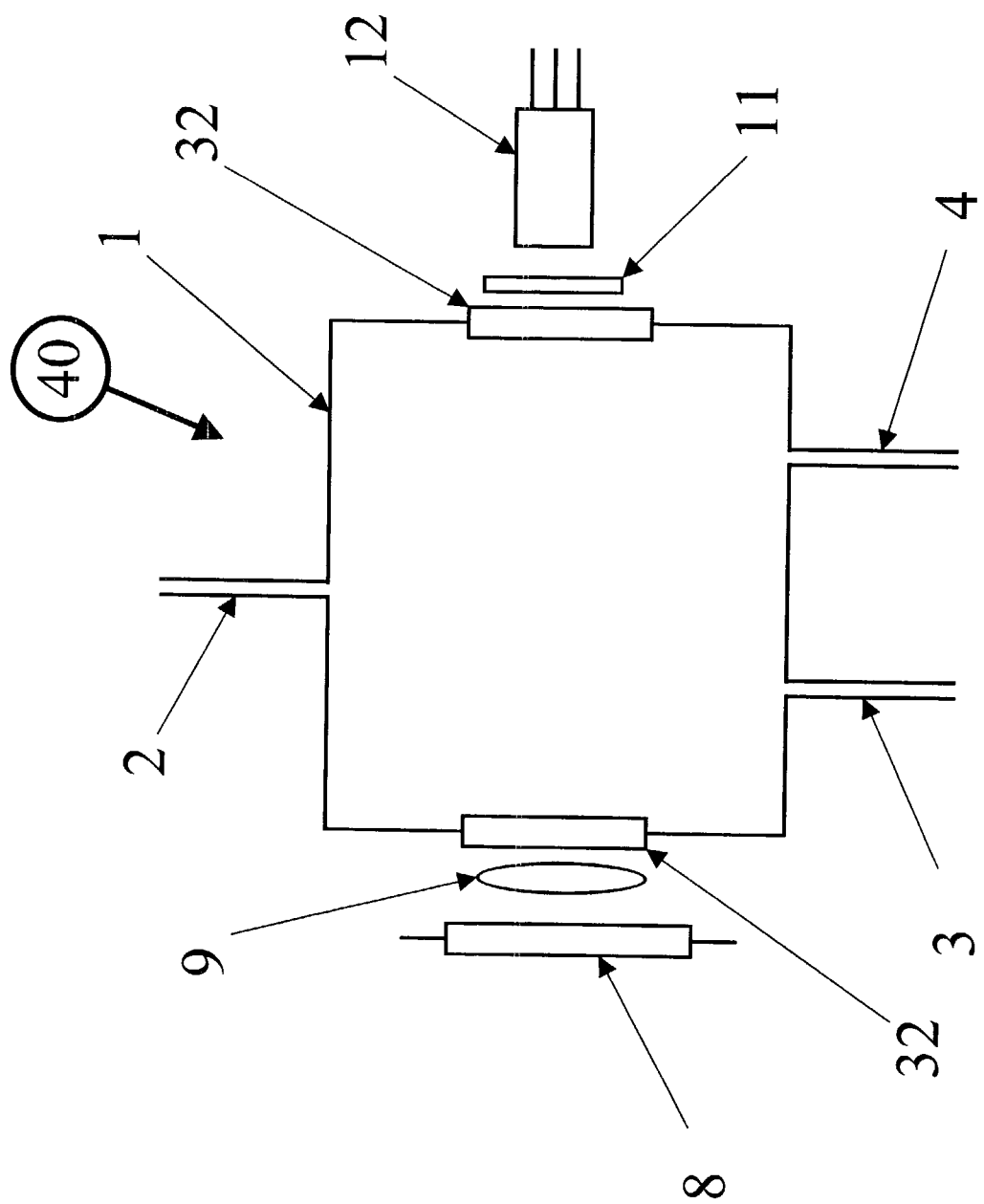
FIG. 4 is a schematic layout of an alternate embodiment chamber using a UV absorption system to detect concentrations of $O_3$.

Referring next to FIG. 4 the batch systems of FIGS. 1, 2, 3 may be configured to use an ultra-violet (UV) light sensing meter to detect ozone concentration. The batch apparatus 40 represents this UV system. A UV light source 8 emits UV light through an optional lens 9 which transmits the focused light rays through left window 32 in the test chamber 1. The light travels through the test chamber 1 and is absorbed by the O$_3$ to decrease the light intensity according to the Beer-Lambert law. The light then travels out right window 32 through an optional filter 11 and into a photodetector 12. The photodetector 12 may be a photodiode or a photomultiplier tube known in the art.

Figure 5:
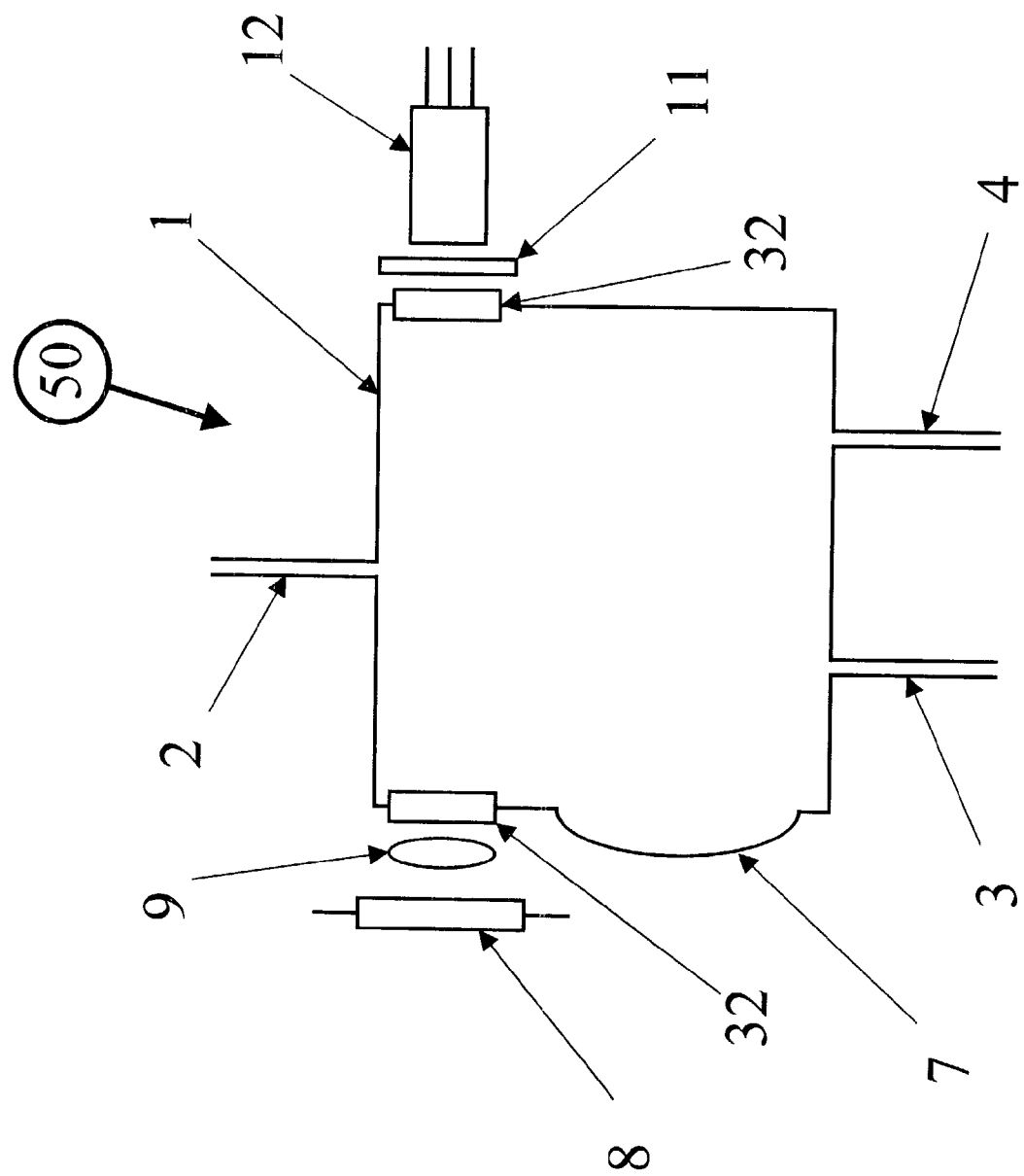
FIG. 5 is a schematic layout of an alternate embodiment chamber using a combination of the flexible wall and the UV absorption system.

Referring next to FIG. 5 a home use batch apparatus 50 comprises a flexible membrane 7 in a test chamber 1 plus a UV measurement system as described in FIG. 4.

Figure 6:
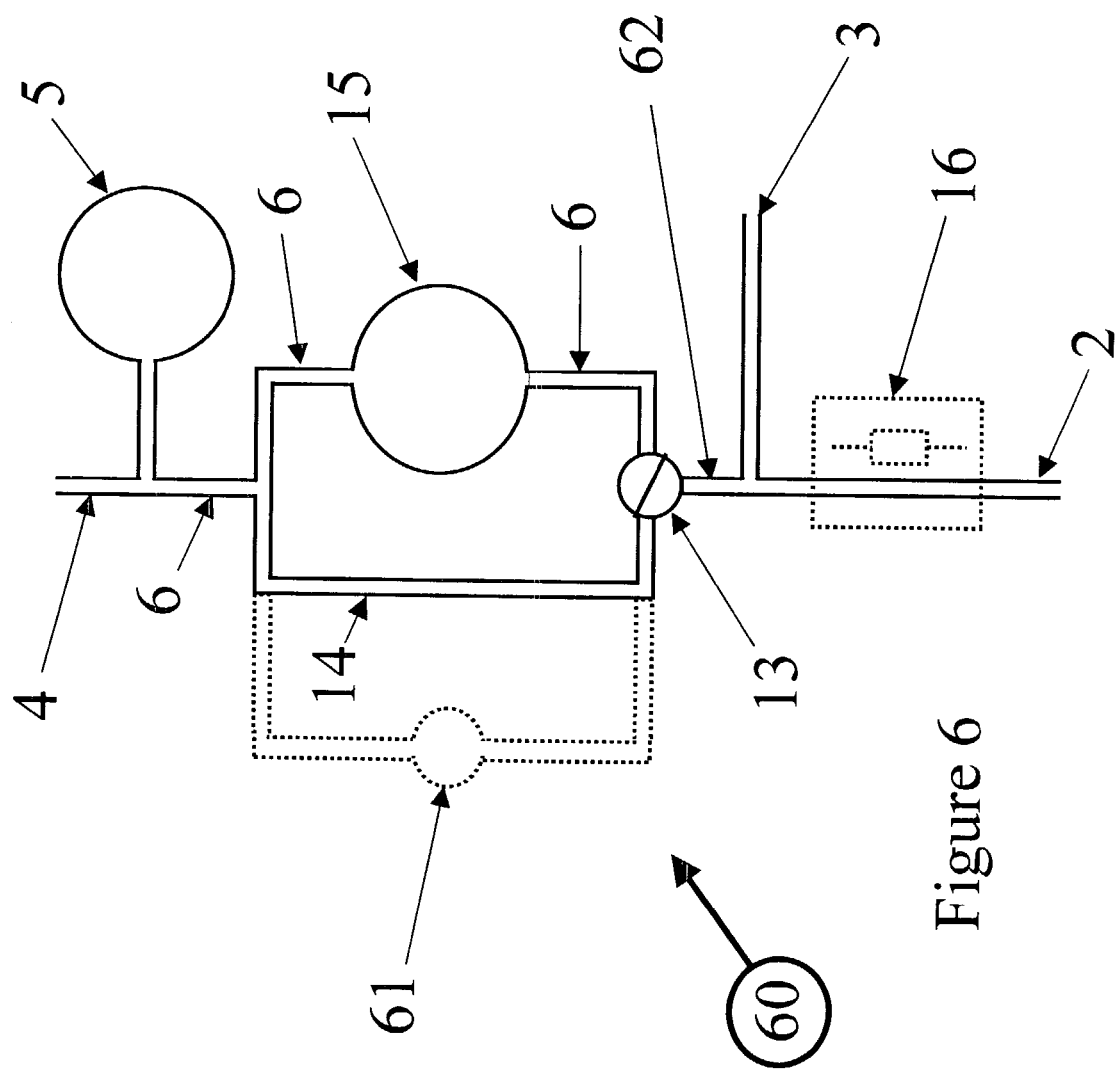
FIG. 6 is a schematic layout of an alternate embodiment test apparatus using a continuously flowing gas stream measurement technique which provides batch data analysis.
Figure 7:
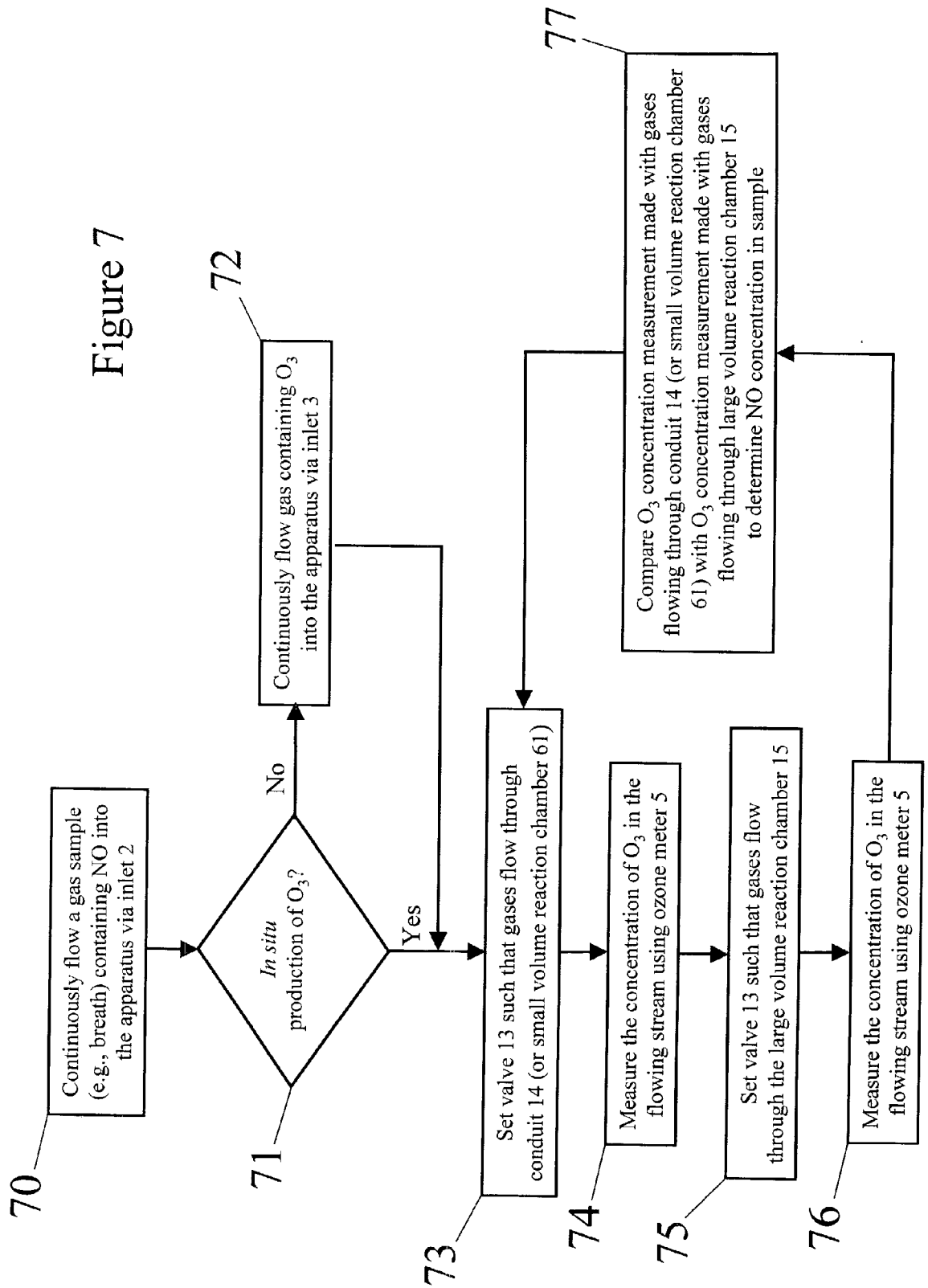
FIG. 7 is a flow chart of the basic steps to practice the invention using the FIG. 6 apparatus.

Referring next to FIGS. 6, 7 a continuously flowing gas system 60 is shown. The designation "conduit 14" represents the common pathway volume of the O$_3$+air sample without the large volume reaction chamber 15. The theory of operation is that when a test sample or a continuously flowing sample is sent through conduit 14, little or no O$_3$ reacts with NO, and a baseline O$_3$ measurement is established. When a second test sample or a continuously flowing sample is sent through the large volume reaction chamber 15, practically all of the NO is reacted with O$_3$, thus yielding an accurate NO concentration by a comparison of the two measurements. Optimally, the volume of conduit 14 would be zero, so that 0% reaction of O$_3$+NO would occur while the gases transit this pathway, and the volume of reaction volume 15 would be infinite, so that this reaction would proceed to 100% completion. In this simple model, the concentration of NO would then be the simple difference of the O$_3$ concentrations measured by ozone meter 5.

An alternative embodiment to conduit 14 is the small volume reaction chamber 61. The actual volume of chamber 61 is chosen such that there is sufficient time for potentially interfering compounds to react to a large extent with O$_3$ but not enough reaction time for a significant amount of NO to react with O$_3$. Examples of potential interferences whose effects can be eliminated in this way include some alkenes such as ethylene.

In practice, the conduit 14 may actually be a small volume reaction chamber 61 which serves to cancel out the effects of interfering compounds by allowing those compounds to react with an approximately equal amount of ozone in the conduit (or small reaction volume) and the large volume reaction volume.

A sample inlet 2 contains an unknown NO concentration perhaps from a long human breath exhalation. Ozone is supplied either by an inlet 3 or an in-line O$_3$ generator 16 which could be a photochemical reactor. Valve 13 diverts the combined flow from inlets 2 and 3 to either the conduit 14 (or small volume reaction chamber 61) or the large volume reaction chamber 15 via connecting tube 6. The ozone meter 5 is connected to the exhaust port 4.

Step 70 of FIG. 7 shows a test sample of gas initiated into sample inlet 2. Decision step 71 provides for either a continuous O$_3$ flow through inlet 3 in step 72, or for in situ production of O$_3$ with the O$_3$ generator 16. In step 73, O$_3$ and the test sample are sharing the tube at tube segment 62, and the valve 13 is first set to flow the mixture through the conduit 14 (or small volume reaction chamber 61). Step 74 measures the output from the conduit 14 (or small volume reaction chamber 61) with ozone meter 5.

Step 75 sets valve 13 to the large volume reaction chamber 15 so that a second O$_3$ measurement can be made in step 76. Step 77 compares the two measurements to determine the NO concentration in the continuous sample of gas. Repeat measurements can be made by returning to step 73.

Figure 8:
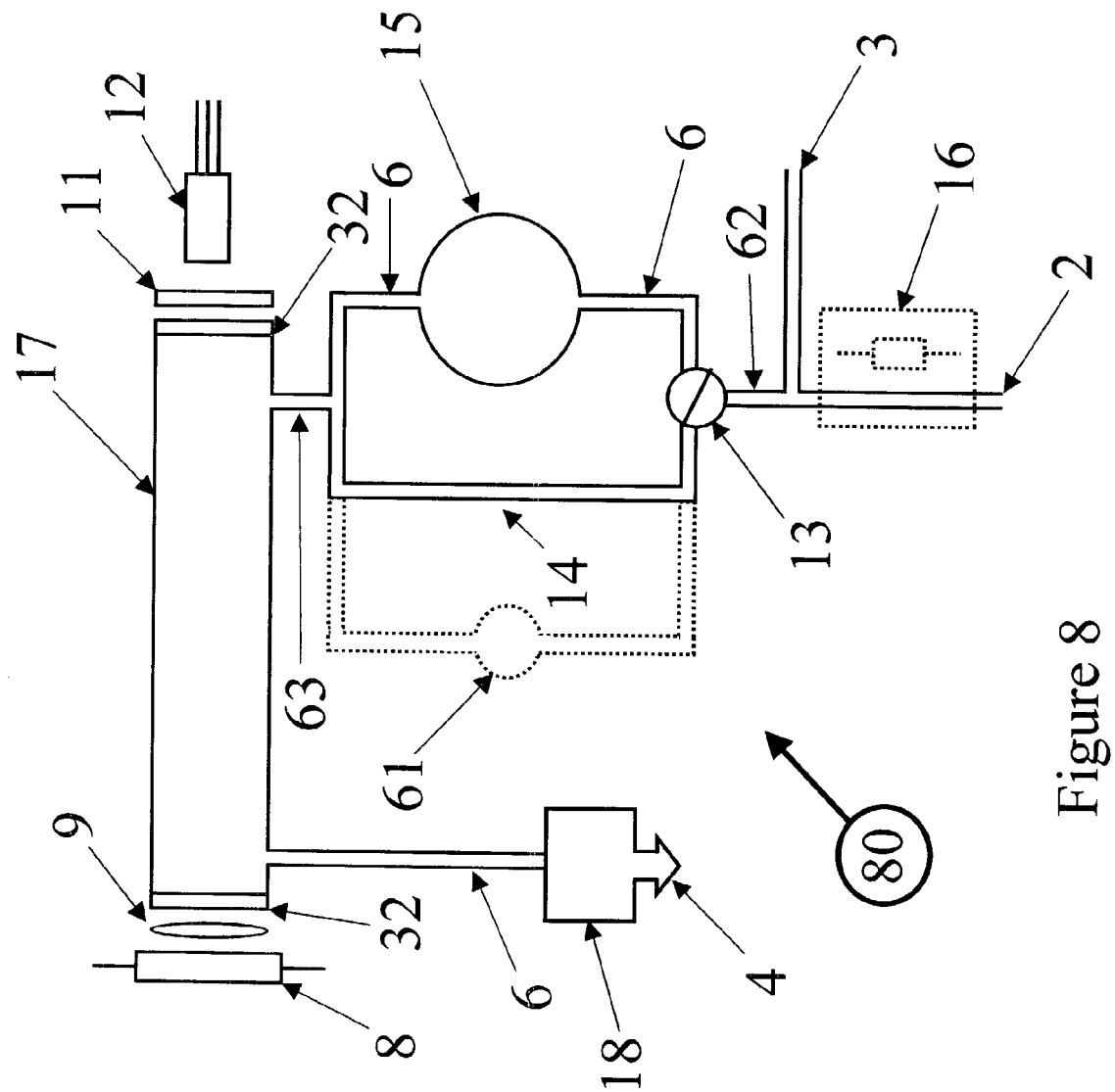
FIG. 8 is a schematic layout of the FIG. 6 apparatus using a UV absorption $O_3$ measurement technique, the initial prototype.

Referring next to FIG. 8 the same procedure described by FIG. 7 can be used. The generic ozone meter 5 of FIG. 6 has been replaced with a detection cell 17 connected at tube segment 63. The known means to measure O$_3$ in the detection cell 17 consists of shining a UV light 8 through an (optional) lens 9, through the left UV transparent window 32, through the test sample in detection cell 17, out the right UV transparent window 32, through the (optional) optical filter 11, and into photodetector 12 (a photodiode, photomultiplier tube or the equivalent). An optional gas pump 18 can be used to draw the gas through the apparatus.

Figure 9:
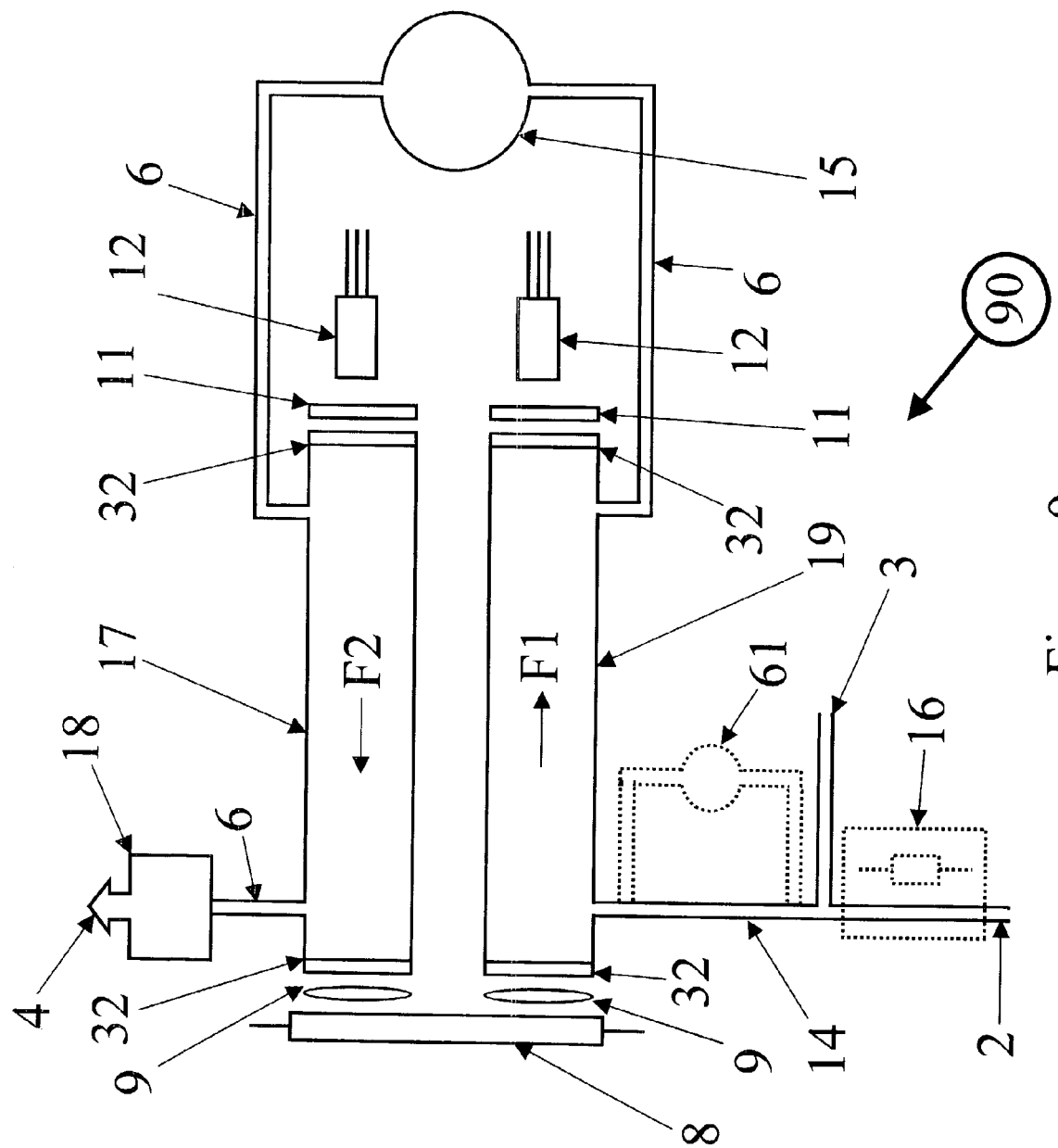
FIG. 9 is a schematic layout of an enhanced continuous flow apparatus which constantly measures $O_3$ concentration in the test gas in a pre- and post-reaction chamber.
Figure 10:
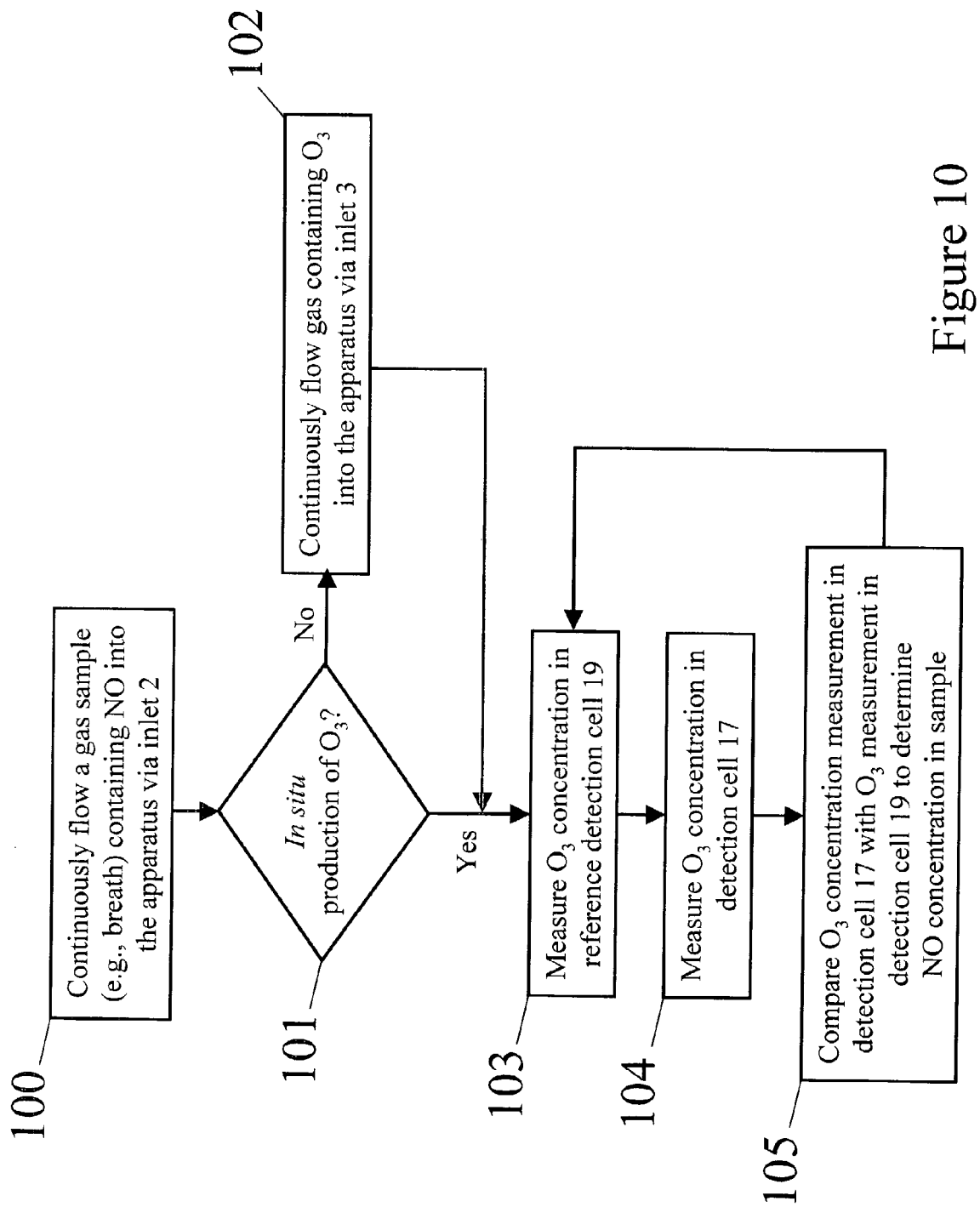
FIG. 10 is a flow chart of the steps to practice the invention with the FIG. 9 apparatus.

Referring next to FIGS. 9, 10 a continuous flow system 90 uses the small volume reaction chamber/large volume reaction chamber concept, but sends the same gas sample through a first measurement in reference detection cell 19 and a second measurement in detection cell 17. Arrows F1, F2 indicate the gas flow directions.

Step 100 initiates a continuous gas sample into inlet 2. Decision step 101 provides for either a continuous O$_3$ flow into inlet 3, or in situ O$_3$ production in O$_3$ generator 16. The test sample and O$_3$ mixture at conduit 14 (or small volume reaction chamber 61) are fed into the reference detection cell 19 and the O$_3$ concentration is measured in step 103. The same gas sample travels into the large volume reaction chamber 15, and the O$_3$ and NO react. Step 104 measures the reacted gas mixture in detection cell 17.

Step 105 does the comparison of the two measurements to determine the NO concentration in the test sample. Repeat measurements are done by returning to step 103.

Figure 11:
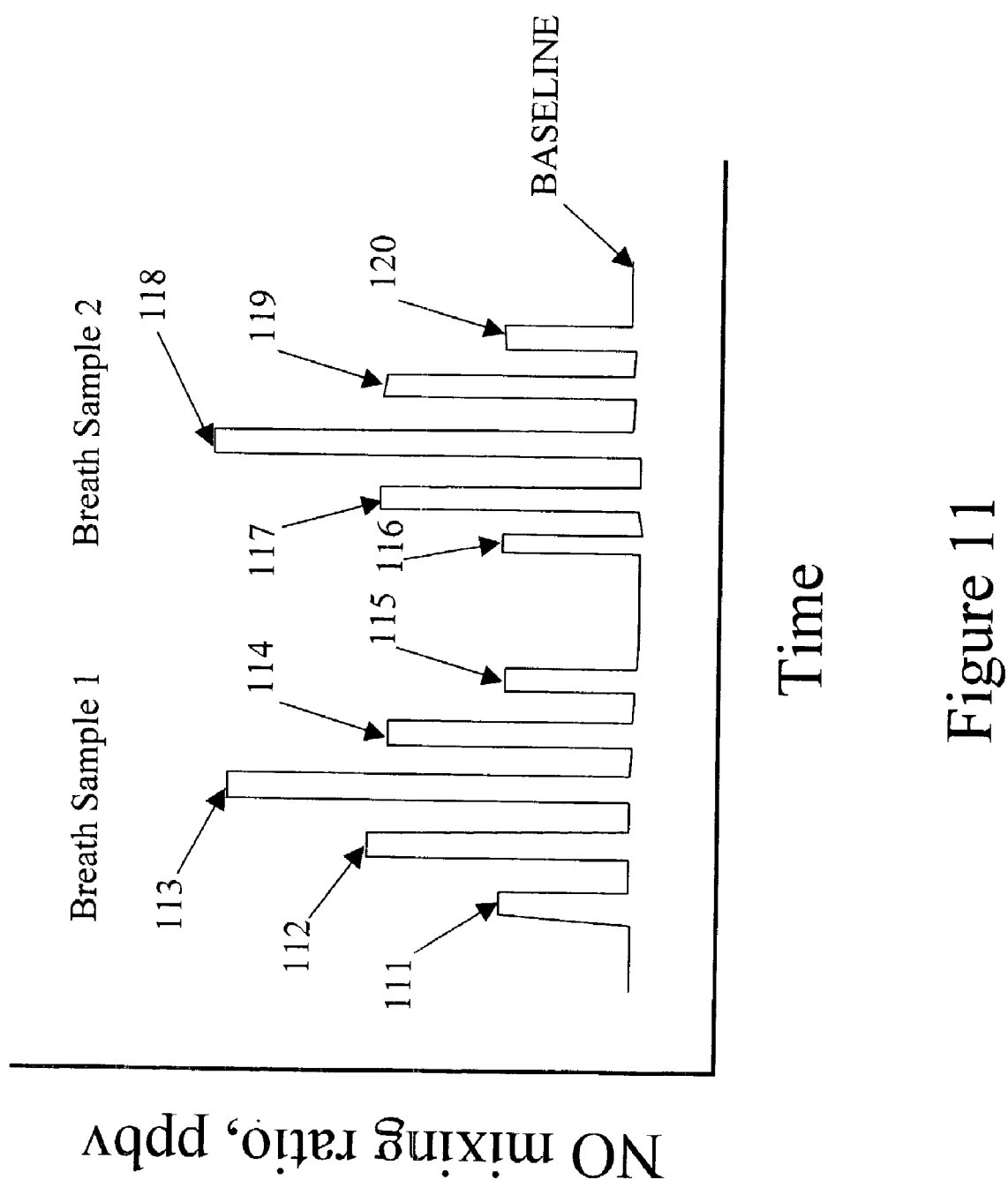
FIG. 11 is a sample chart of a theoretical test result using the FIG. 8 apparatus.

Referring next to FIG. 11, a theoretical response to two samples of human breath is shown using the NO detection system 60 of FIG. 6. The baseline signal is obtained when the solenoid valve 13 is positioned such that the ozone mixed with sample air passes through conduit 14 (or the small volume reaction chamber 61). The positive excursions in signal (points 111–120) are obtained when the solenoid valve 13 is positioned such that ozone mixed with sample air passes through the large volume reaction chamber. For this NO detection system, the NO measurement in breath is intermittent, where the measurements return to "BASELINE" after each breath sampling period 111–120. However, if the baseline is sufficiently stable, the breath sampling period could cover the entire time of expiration of an entire human breath.

Figure 12:
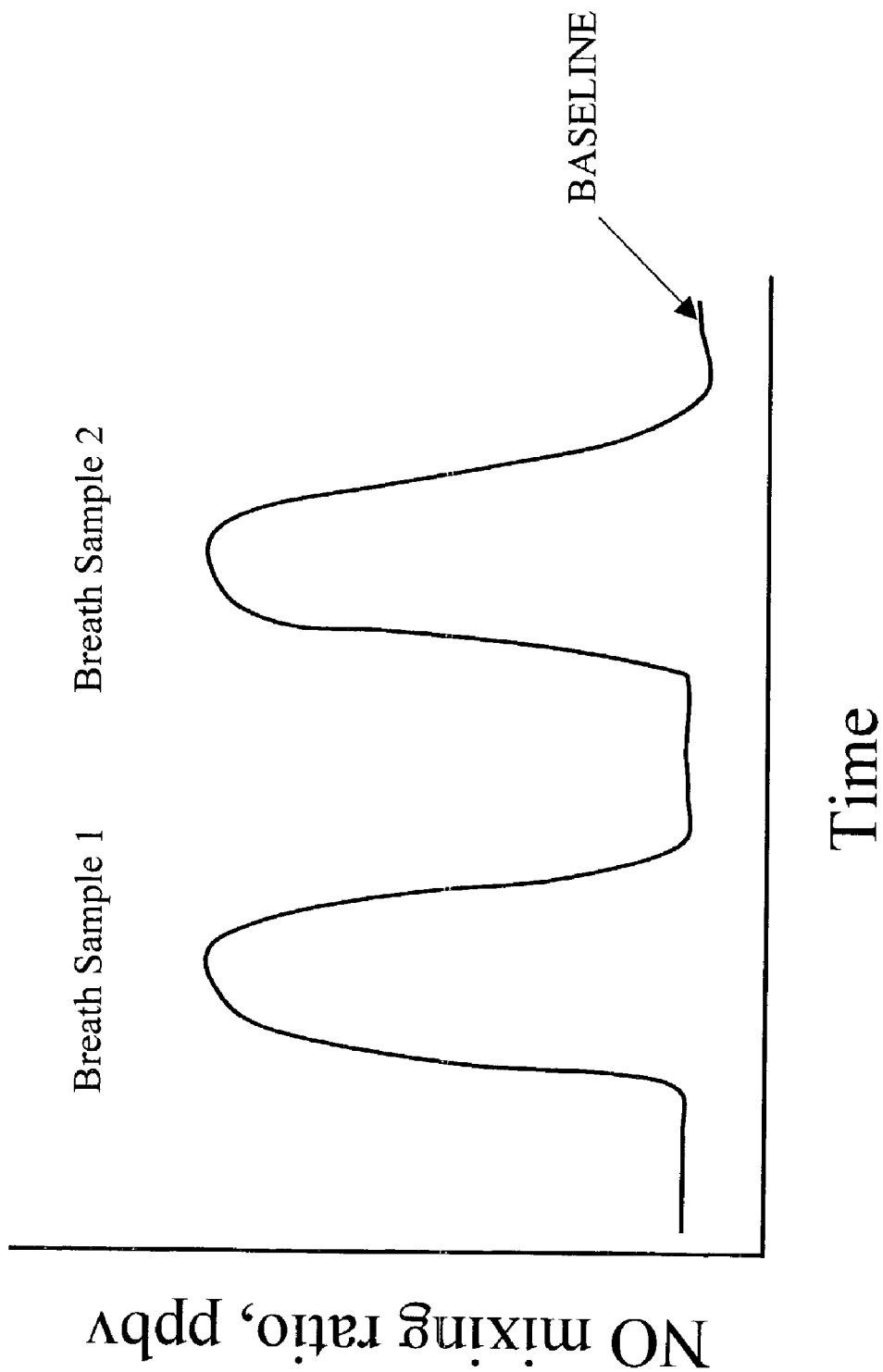
FIG. 12 is a sample chart of a theoretical test result using the FIG. 9 apparatus.

Referring next to FIG. 12, the theoretical response to two samples of human breath is shown using the NO detection system 90 of FIG. 9. For this NO detection system, the NO measurement is continuous because the "BASELINE" is continuously measured in detection cell 17 and its value subtracted from the continuously measured sample value in reference cell 19.

Figure 13:
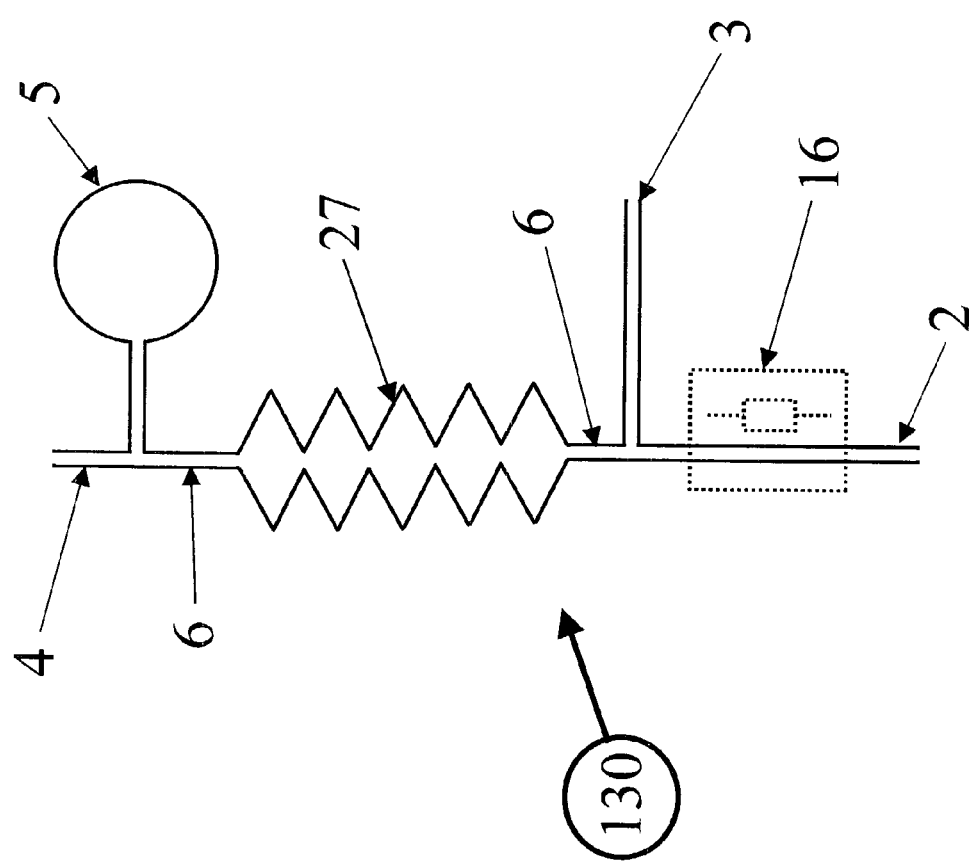
FIG. 13 is a schematic layout of an alternate embodiment test apparatus using a continuous flowing gas stream measurement technique with a variable reaction volume.

Referring next to FIG. 13, the NO detection system 130 is an alternative to the NO detection system 60 of FIG. 6. In this NO detection system the solenoid valve, conduit and large volume reaction volume are replaced by a single variable volume reaction chamber 27 (such as bellows or combination of piston and cylinder) that can be compressed to form a conduit (or small volume reaction chamber) and expanded to form a large volume reaction chamber. Shrinking and expanding the variable volume reaction chamber 27 of FIG. 13 is equivalent to switching the solenoid valve 13 of FIG. 6. When a bellows is used, this NO detection system has the advantage that the surfaces exposed to the ozone mixed with gas sample are the same for the conduit (or small volume reaction chamber) and large volume reaction chamber. This could be important because it is known in the art that ozone can be decomposed on surfaces, and a difference in ozone destruction at the conduit (or small volume reaction chamber) and large reaction volumes could result in a false NO signal.

Figure 14:
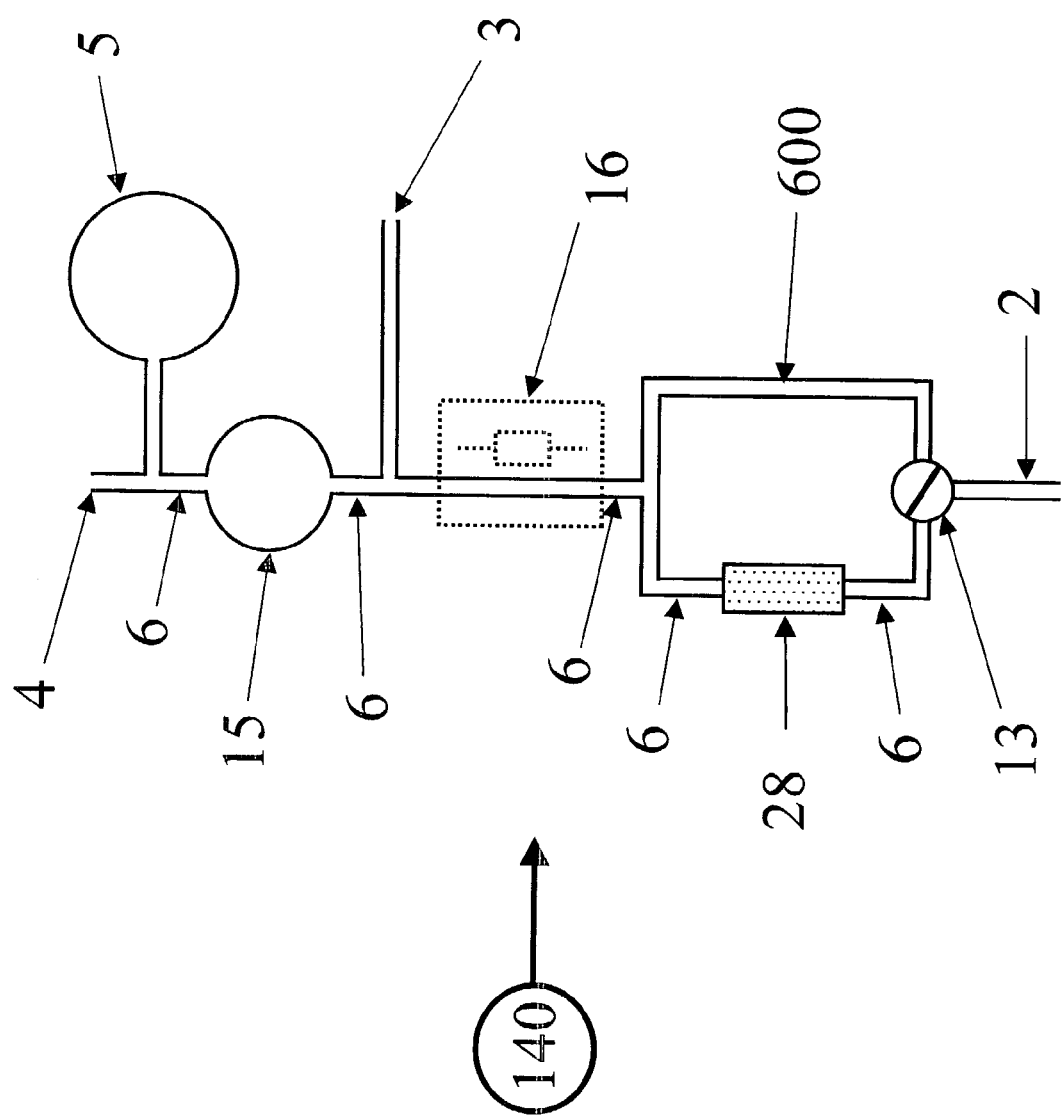
FIG. 14 is a schematic layout of an alternate embodiment test apparatus using a continuously flowing gas stream measurement technique with a NO scrubber which provides batch data analysis.
Figure 15:
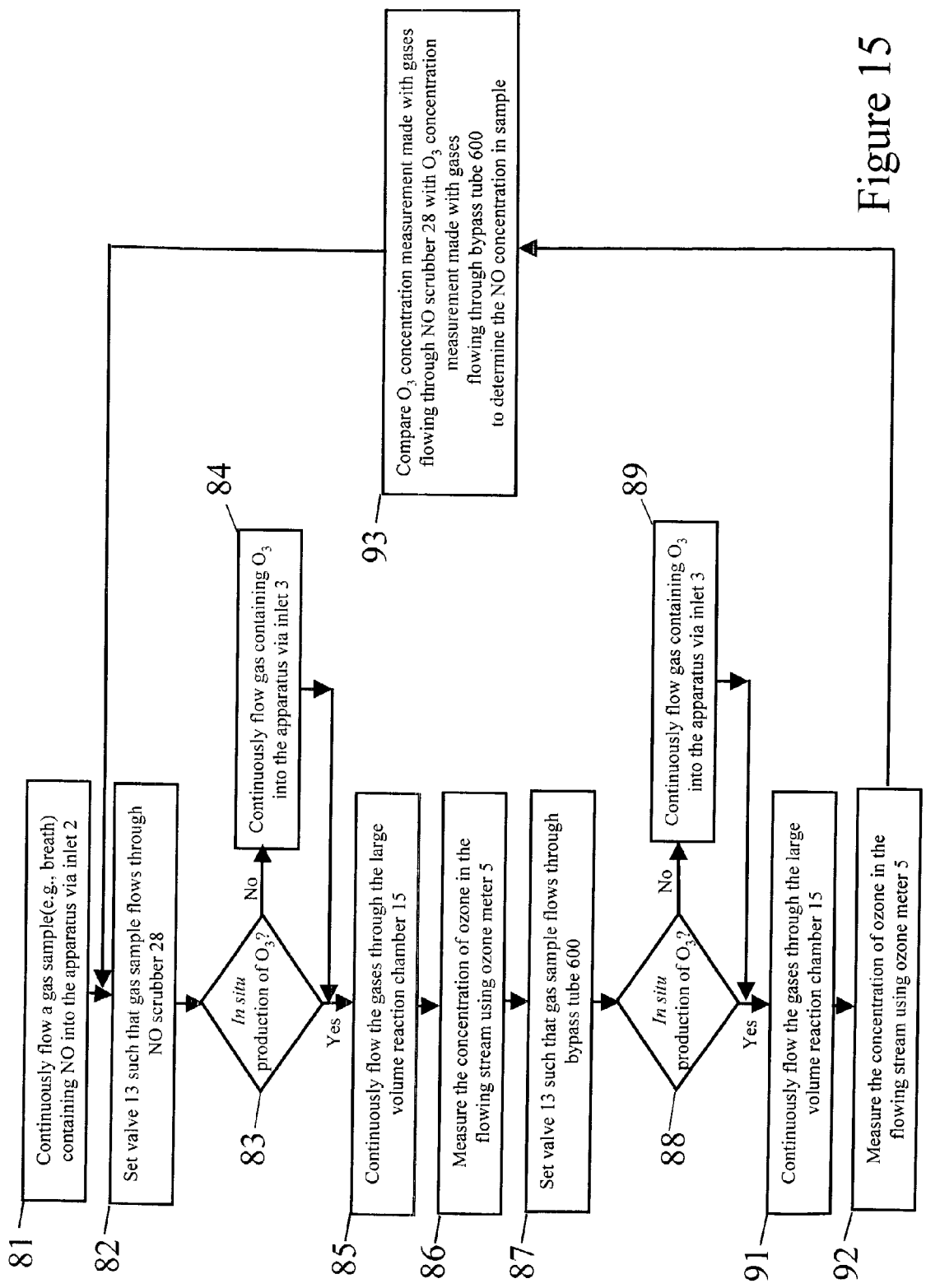
FIG. 15 is a flow chart of the steps to practice the invention with the FIG. 14 apparatus.

Referring next to FIGS. 14, 15 the NO detection system 140 is another alternative to the NO detection system 60 of FIG. 6. In this NO detection system, a solenoid valve 13 is alternately switched such that a gas sample entering inlet 2 (Step 81) passes through either bypass tube 600 (Step 87) or NO scrubber 28 (Step 82). The NO scrubber 28 contains materials known in the art to remove NO from the gas sample. Following the connecting tubing or scrubber, ozone is added to the gas sample through inlet 3 (Step 84, 89) or alternatively is produced directly in the flowing stream using photochemical reactor 16 (Steps 83, 88). Next, the mixture of gas sample and ozone flows through the large volume reaction chamber 15 to allow NO to react with $O_3$ (Steps 85, 91) and is then detected using the generic ozone meter 5 (Steps 86, 92). The NO concentration is calculated as the ozone concentration measured when the gas sample passes through the NO scrubber 28 minus the ozone concentration measured when the gas sample passes through bypass tube 600 (Step 93). A correction can be applied if the reaction time is insufficient for NO and $O_3$ to react completely in the large volume reaction chamber.

Figure 16:
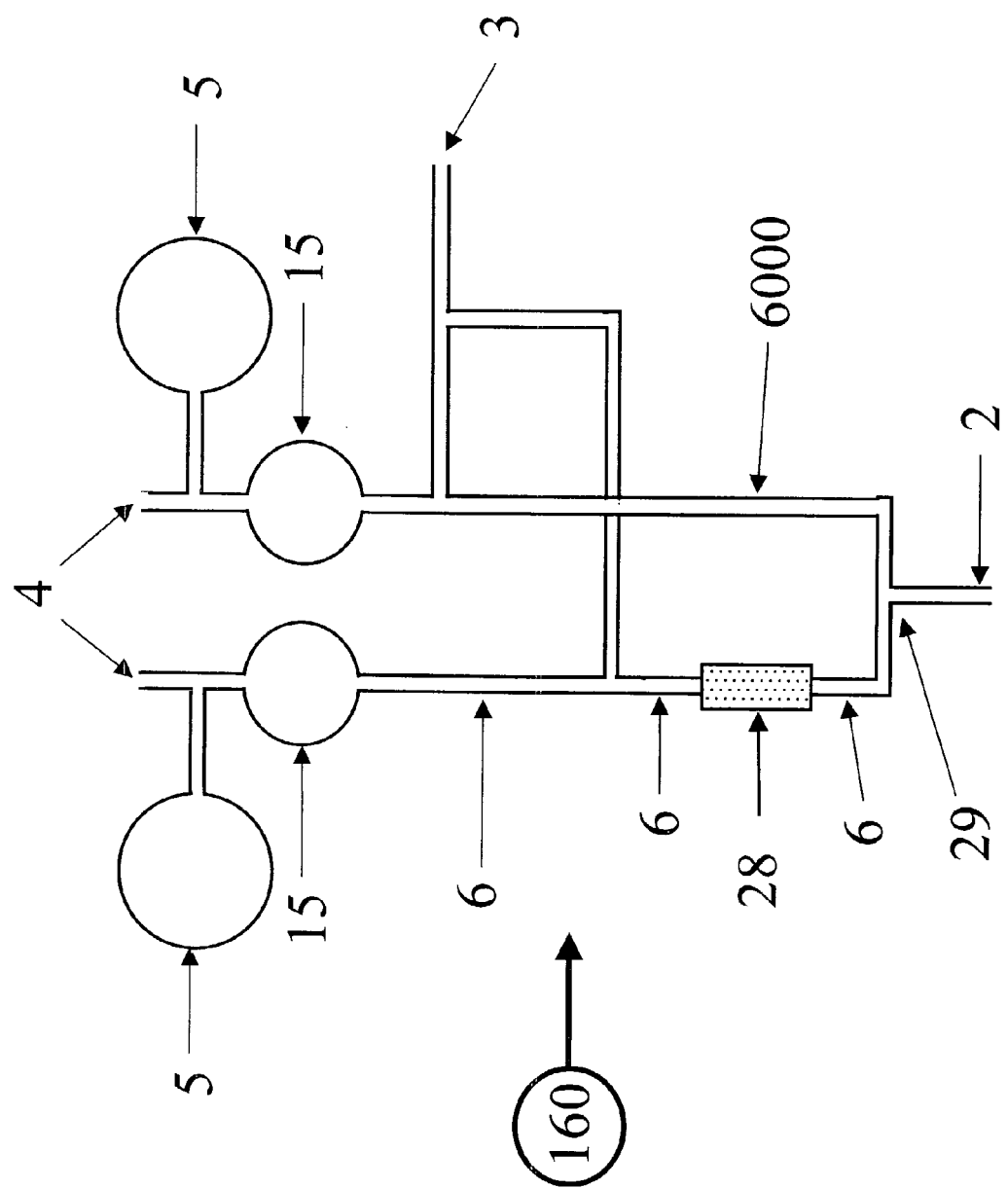
FIG. 16 is a schematic layout of an alternate embodiment test apparatus using a continuous flowing gas stream measurement technique with a NO scrubber that provides continuous data analysis.
Figure 17:
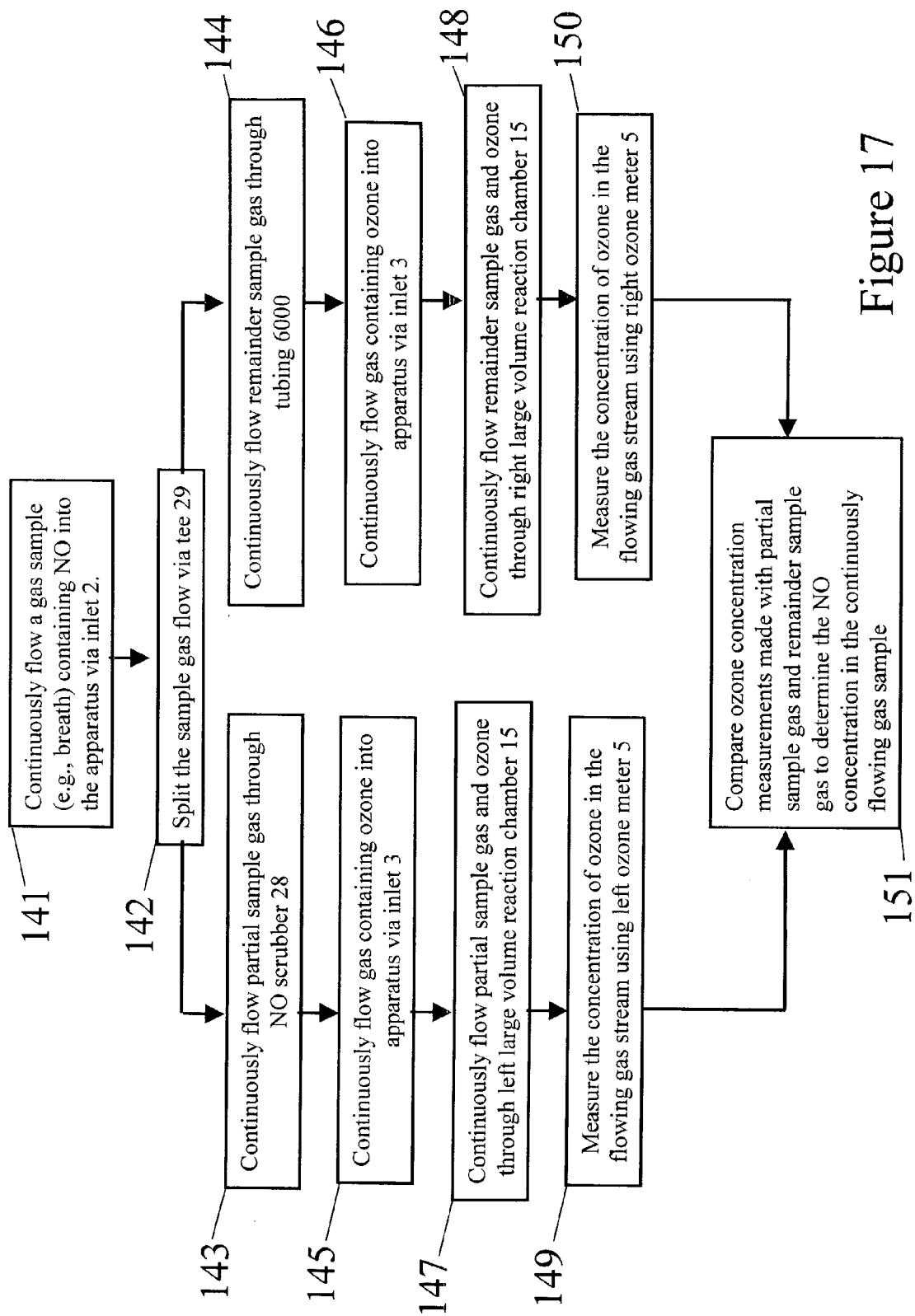
FIG. 17 is a flow chart of the steps to practice the invention with the FIG. 16 apparatus.

Referring next to FIGS. 16, 17 the NO detection system 148 is another alternative to the NO detection system 60 of FIG. 6. In this NO detection system, a continuously flowing gas sample entering the system through sample inlet 2 (Step 141) is split into two continuously flowing gas streams (Step 142). One of the parts of the continuously flowing gas stream flows through a NO scrubber 28 (Step 143). Gas containing ozone is continuously added to this partial continuously flowing gas sample through inlet 3 (Step 145). The partial continuously flowing gas sample+ozone then flows through the left large volume reaction chamber 15, which allows ozone to react with any interfering species which may be present in the continuously flowing gas sample (Step 147), and also compensates for the time required for the remainder of the continuously flowing gas sample+ozone to flow through the apparatus. It is well known in the art that this latter timing issue can also be addressed through electronic manipulation of the measurement data. After passing through the large volume reaction chamber 15, the ozone in the continuously flowing gas sample+ozone is detected using left generic ozone meter 5 (Step 149), and the partial continuously flowing gas sample+ozone exit the instrument via left outlet 4. Simultaneously to the aforementioned steps involving the partial continuously flowing gas sample, the remainder continuously flowing gas sample passes through bypass tube 6000 (Step 144). Gas containing ozone, split from the source supplying the aforementioned partial continuously flowing gas sample is continuously added to the remainder continuously flowing gas sample through inlet 3 (Step 146). The remainder continuously flowing gas sample+ozone then flows through the right large volume reaction chamber, where the ozone reacts with the NO present in the remainder partial continuously flowing gas sample (Step 148). The ozone is then detected using right generic ozone meter 5 (Step 150), and the remainder continuously flowing gas sample+ozone exit the instrument via right outlet 4. The NO concentration in the continuously flowing gas sample is calculated as the difference between this measurement and that obtained by left generic ozone meter 5 (Step 151). A correction can be applied if the reaction time is insufficient for NO and $O_3$ to react completely in the right large volume reaction chamber.

EXAMPLE

Figure 18:
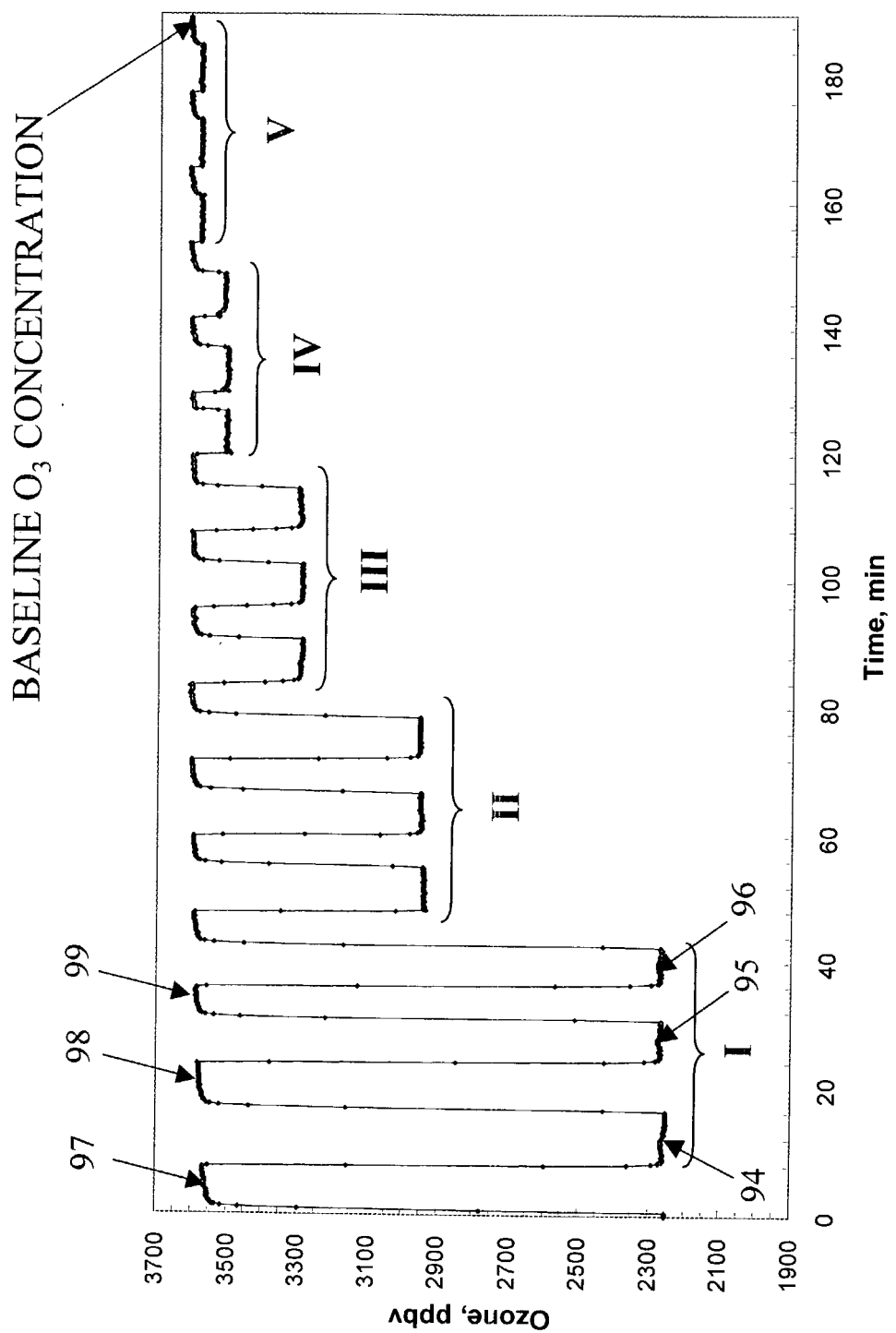
FIG. 18 is an actual chart of data obtained using apparatus 80 of FIG. 8.

Referring next to FIG. 18, experimental results for measurements of NO are shown for the NO detection system 80 of FIG. 8. In this experiment only the large volume reaction chamber 15 was used, and the baseline ozone was measured by removing the sample NO from inlet 2 rather than by passing the ozone and sample air mixture through the small reaction volume. Ozone was generated by use of a photochemical reactor (not shown but located directly on inlet 3) and admitted to the system via inlet 3. Measurements of ozone were made every 10 seconds by absorbance of light having a wavelength of 254 nm. With no sample air added, the ozone concentration was in the range 3550 to 3650 parts-per-billion by volume (ppbv); see "BASELINE $O_3$ CONCENTRATION." The total flow rate of sample air and $O_3$ was 0.95 L/min, the volume of the large volume reaction chamber was 100 $cm^3$, and the total pressure was 0.71 atm, resulting in a reaction time of 4.5 seconds. Using the well-known rate constant for the NO+$O_3$ reaction of $1.8 \times 10^{-14}$ $cm^3$ $molec^{-1}$ $s^{-1}$, it is calculated that 99.4% of the NO in the sample reacts with $O_3$. Air was sampled three times each for five different NO concentrations labeled groups I, II, III, IV, V. Ozone concentrations declined each time sample air was admitted to the system, corresponding to measured NO concentration group I=1317, group II=651; group III=309, group IV=97; group V=31 ppbv for the five different air samples tested.

For example, the formula to obtain the NO concentration of 1317 in group 1 is to subtract the average of readings 94, 95, 96 from the average of the baseline at points 97, 98,99. The measurement is then corrected by multiplying by 1.006 to correct for the 0.6% of NO that does not react within the large volume reaction chamber.

Although the present invention has been described with reference to disclosed embodiments, numerous modifications and variations can be made and still the result will come within the scope of the invention. No limitation with respect to the specific embodiments disclosed herein is intended or should be inferred. Each apparatus embodiment described herein has numerous equivalents.

We claim:

1. A method to determine a NO concentration in a test sample in a reaction chamber, wherein said concentration is in the range of parts per million or less by volume, the method comprising the steps of:
- treating said test sample with a gas sample having a known concentration of ozone a priori exceeding a concentration of NO in the test sample, whereby the ozone and NO react to form a product mixture comprising $O_2$ and $NO_2$;
- allowing the reaction of ozone and NO to go to completion;
- measuring a concentration of ozone in said product mixture; and
- quantifying the concentration of NO in said test sample by calculating an ozone difference between said gas sample and said product mixture.

2. The method of claim 1, wherein the gas sample is air and wherein ozone is added to the air prior to measuring the ozone concentration of said gas sample.

3. The method of claim 1, wherein the test sample comprises a human breath.

4. The method of claim 3, wherein the reaction mixture is formed in a reaction chamber comprising a flexible wall.

5. The method of claim 4 further comprising the step of evacuating the reaction chamber prior to repeating said method by adding one or more subsequent test samples comprising NO to said evacuated reaction chamber.

6. The method of claim 1, wherein the steps of measuring the concentration of ozone in said gas sample and the concentration of ozone in said reaction mixture further comprise using an ultraviolet absorbance spectrometer.

7. A method to determine a NO concentration in a test sample in a reaction chamber, wherein said concentration is in the range of parts per million or less by volume, the method comprising the steps of:
- treating said test sample with a gas sample having a known concentration of ozone a priori exceeding a concentration of NO in the test sample, whereby the ozone and NO react to form a product mixture comprising $O_2$ and $NO_2$;
- measuring a concentration of ozone in said product mixture;
- quantifying the concentration of NO in said test sample by calculating an ozone difference between said gas sample and said product mixture; and
- applying a correction factor to calculate a concentration of NO when the reaction of ozone and NO does not achieve completion.

8. The method of claim 7, wherein the correction factor when $[O_3]>>[NO]$ has the formula $k_{correction}=1/\{1-\exp(-k[O_3]t)\}$,
wherein $[NO]_{sample}=k_{correction}[NO]_{measured}$, $[NO]_{measured}$ comprises a measured concentration of NO, $[NO]_{sample}$ comprises a concentration of actual NO in said gas sample, $[O_3]$ comprises the concentration of $O_3$, t is the contact time between NO and $O_3$, and k is the second order rate constant for the gas-phase reaction of NO with ozone.

9. The method of claim 7, wherein the test sample comprises a human breath.

10. The method of claim 9, wherein the steps of measuring the concentration of ozone in said gas sample and the concentration of ozone in said reaction mixture further comprise using an ultraviolet absorbance spectrometer.

11. The method of claim 7, wherein the reaction mixture is formed in a reaction chamber comprising a flexible wall.

12. The method of claim 11 further comprising the step of evacuating the reaction chamber prior to repeating the steps of said method by adding one or more subsequent test samples comprising NO to said evacuated reaction chamber.

13. A method to determine a concentration of a reactive nitrogen oxide capable of producing NO in a concentration of parts per million or less by volume, in a sample of gas, the method comprising:
- reacting the sample of gas comprising the reactive nitrogen oxide to produce a mixture comprising NO;
- providing a gas comprising a baseline concentration of ozone a priori exceeding a concentration of produced NO to a reaction chamber;
- introducing the mixture comprising NO into said reaction chamber, whereby the ozone and NO form a product mixture comprising $O_2$ and $NO_2$;
- measuring a concentration of ozone in said product mixture comprising $O_2$ and $NO_2$; and
- quantifying the concentration of the reactive nitrogen oxide in said gas sample by calculating an ozone difference between said baseline ozone value and the ozone measured in said product mixture.

14. The method of claim 13, wherein the reactive nitrogen oxide is selected from the group consisting of $NO_2$, $NO_3$, $NO_x$, $NO_y$, $N_2O_5$, $HNO_2$, $HNO_3$, $HNO_4$, peroxyacetyl nitrate (PAN), and $ClNO_3$; wherein $NO_x$ is a mixture of NO and $NO_2$ and $NO_y$ is a combination of reactive nitrogen oxides.

15. A method to determine a NO concentration in a continuously flowing gas sample, wherein said concentration is in the range of parts per million or less by volume, the method comprising the steps of:
- mixing said continuously flowing gas sample with a continuous flow of ozone, wherein a concentration of ozone in a continuously flowing gas mixture a priori exceeds a concentration of NO;
- introducing said continuously flowing gas mixture into an apparatus having a first chamber and a conduit in connection with each other via a connection means;
- wherein said first chamber has a sufficiently large volume to enable a substantially large fraction of the NO to react with ozone while passing through the first chamber but a sufficiently small volume to minimize a reaction with slower reacting potential interfering compounds;
- engaging the connection means to cause the continuously flowing gas mixture to pass through the conduit and to bypass the first chamber, wherein said conduit has a sufficiently small volume whereby only a small fraction of NO reacts with ozone while passing through the conduit;
- measuring the concentration of ozone in or downstream of said conduit, thereby establishing a first ozone value;
- engaging the connection means to cause the continuously flowing sample gas comprising NO to pass through the first chamber and to bypass the conduit;
- measuring the concentration of ozone in or downstream of said first chamber, thereby establishing a second ozone value; and
- quantifying the concentration of NO in said continuously flowing gas sample by calculating an ozone difference between said first and second ozone values.

16. The method of claim 15, wherein the conduit further comprises a second chamber having a sufficiently small volume to enable potential interfering compounds having fast reactions with ozone to react nearly completely with ozone while passing therethrough, whereby NO reacts only to a small extent with ozone while passing therethrough.

17. The method of claim 15, wherein the steps of measuring the first and second ozone values further comprise using an ultraviolet absorbance spectrometer.

18. The method of claim 15, wherein the ozone added to said first chamber is produced in situ.

19. A method to determine a NO concentration in a continuously flowing gas sample, wherein said concentration is in the range of parts per million or less by volume, the method comprising the steps of:
  mixing said continuously flowing gas sample with a continuous flow of ozone, wherein a concentration of ozone in a continuously flowing gas mixture a priori exceeds a concentration of NO;
  introducing said continuously flowing gas mixture into a reference detection cell;
  measuring the concentration of ozone in said reference detection cell, thereby establishing a reference ozone value;
  passing the continuously flowing gas mixture into a reaction chamber, wherein said reaction chamber has a sufficient volume to enable a substantially large fraction of the NO to react with ozone to form a product mixture comprising $O_2$ and $NO_2$ while passing through the reaction chamber but small enough that slower reacting potential interfering compounds do not substantially react;
  introducing the product mixture into a detection cell;
  measuring a concentration of ozone in said detection cell; and
  comparing the reference ozone value and ozone concentration measured in said detection cell to determine a concentration of NO in the continuously flowing sample gas.

20. The method of claim 19 further comprising the step of continuously flowing the gas sample comprising NO into a small volume reaction chamber prior to introducing said mixture into the reference detection cell, said small volume reaction chamber having a sufficiently small volume to enable potential interfering compounds having fast reactions with ozone to react nearly completely with ozone while passing therethrough and where NO reacts only to a small extent with ozone while passing therethrough.

21. The method of claim 19, wherein the steps of measuring the concentration of ozone in each of the reference and detection cells further comprise using an ultraviolet absorbance spectrometer.

22. The method of claim 19, wherein said ozone is produced in situ.

23. A method to determine a NO concentration in a continuously flowing sample of gas, wherein said concentration is in the range of parts per million or less by volume, the method comprising the steps of: chamber;
  mixing said continuously flowing sample of gas with a continuous flow of ozone, wherein a concentration of ozone in a continuously flowing gas mixture a priori exceeds a concentration of NO;
  passing said continuously flowing sample gas through a variable volume reaction chamber variably positioned to have a sufficiently small volume to enable potential interfering compounds having fast reactions with ozone to react nearly completely with ozone while passing therethrough and where NO reacts only to a small extent with ozone while passing therethrough;
  measuring the concentration of ozone in or downstream of said reaction chamber, thereby establishing a first ozone value;
  passing a continuously flowing sample gas comprising NO through said variable volume reaction chamber variably positioned to have a sufficiently large volume to enable a substantially large fraction of the NO to react with ozone while passing through the chamber but small enough that slower reacting potential interfering compounds do not substantially react;
  measuring the concentration of ozone in or downstream of said reaction chamber, thereby establishing a second ozone value; and
  quantifying the concentration of NO in said continuously flowing gas sample by calculating an ozone difference between said first and second ozone values.

24. The method of claim 23, wherein the variable volume reaction chamber further comprises a bellows.

25. A method of determining a NO concentration in a continuously flowing sample of gas, wherein said concentration is in the range of parts per million or less by volume, the method comprising the steps of:
  mixing said continuously flowing sample of gas with a continuous flow of ozone, wherein a concentration of ozone in a continuously flowing gas mixture a priori exceeds a concentration of NO;
  providing a reaction chamber in serial connection with a scrubber and an upstream connection means;
  passing said continuously flowing gas mixture into said scrubber, wherein said scrubber removes NO from said gas mixture before the gas mixture enters said reaction chamber;
  measuring the concentration of ozone in or downstream of said reaction chamber, thereby establishing at least one ozone value for the scrubbed sample gas;
  engaging the connection means to cause the continuously flowing sample gas mixture comprising NO to bypass said scrubber and enter the reaction chamber;
  wherein said reaction chamber has a sufficiently large volume to enable a substantially large fraction of the NO to react with ozone while passing through the chamber but small enough that slower reacting potential interfering compounds do not substantially react;
  measuring the concentration of ozone in or downstream of said reaction chamber, thereby establishing at least one ozone value for a non-scrubbed gas mixture; and
  quantifying the concentration of NO in said continuously flowing gas sample by calculating an ozone difference between said scrubbed gas and said non-scrubbed gas.

26. The method of claim 25, wherein the steps of measuring the concentration of ozone in the scrubbed gas and the non-scrubbed gas further comprise using an ultraviolet absorbance spectrometer.

27. The method of claim 25, wherein the ozone added to said scrubbed sample gas or said sample gas is produced in situ.

28. A method to determine a NO concentration in a continuously flowing sample of gas, wherein said concentration is in the range of parts per million or less by volume, the method comprising the steps of:
  providing a first reaction chamber in parallel with a second reaction chamber;
  connecting a scrubber in series with said first reaction chamber;
  mixing said continuously flowing sample of gas with a continuous flow of ozone, wherein a concentration of ozone in a continuously flowing gas mixture a priori exceeds a concentration of NO;
  passing a split stream of said continuously flowing sample gas to each of said reaction chambers, wherein said scrubber removes NO from said gas sample stream entering said first reaction chamber;

measuring the concentration of ozone in or downstream of said first reaction chamber, thereby establishing a first reactor ozone value;

measuring the concentration of ozone in or downstream of said second reaction chamber, thereby establishing a second reactor ozone value; and comparing the first and second ozone values to determine a concentration of NO in the continuously flowing sample gas.

29. A method to determine a NO concentration in a human breath sample, wherein said concentration is in the range of parts per million or less by volume the method comprising the steps of:

providing a gas sample comprising a known concentration of ozone a priori exceeding said concentration of NO;

adding a human breath sample comprising NO to said gas sample, whereby the ozone and NO react to form a reaction mixture in a reaction chamber;

allowing a sufficient time to lapse, thereby enabling a destruction or conversion of ozone in the reaction mixture;

measuring a concentration of ozone in said reaction mixture; and quantifying the concentration of NO in said breath sample by calculating an ozone difference between said gas sample and said reaction mixture.

* * * * *